United States Patent [19]

Fong

[11] 4,166,800
[45] Sep. 4, 1979

[54] PROCESSES FOR PREPARATION OF MICROSPHERES

[75] Inventor: Jones W. Fong, Parsippany, N.J.

[73] Assignee: Sandoz, Inc., E. Hanover, N.J.

[21] Appl. No.: 929,517

[22] Filed: Jul. 31, 1978

Related U.S. Application Data

[63] Continuation-in-part of Ser. No. 926,261, Jul. 20, 1978, abandoned, which is a continuation-in-part of Ser. No. 827,710, Aug. 25, 1977, abandoned.

[51] Int. Cl.² .............................................. B01J 13/00
[52] U.S. Cl. ...................................... 252/316; 427/3; 427/212; 424/19; 424/16; 424/32; 427/221

[58] Field of Search ................... 252/316; 427/3, 212, 427/221

[56] References Cited

U.S. PATENT DOCUMENTS

| | | | |
|---|---|---|---|
| 3,317,434 | 5/1967 | Veis | 252/316 |
| 3,427,250 | 2/1969 | Haas et al. | 252/316 |
| 3,703,474 | 11/1972 | Huber | 252/316 |

*Primary Examiner*—Sam Silverberg
*Attorney, Agent, or Firm*—Gerald D. Sharkin; Robert S. Honor; Walter F. Jewell

[57] ABSTRACT

Microspheres, prepared by the low-temperature e.g., $-40°$ to $-100°$ C., phase separation of a polymer and a core material.

45 Claims, No Drawings

PROCESSES FOR PREPARATION OF MICROSPHERES

This application is a continuation-in-part of application Ser. No. 926,261, filed July 20, 1978, now abandoned, which in turn is a continuation-in-part of application Ser. No. 827,710, filed Aug. 25, 1977, now abandoned.

BACKGROUND OF THE INVENTION

This invention relates to microspheres. More particularly it relates to processes for the preparation of microspheres of a polymer and a core material and to products produced thereby. In one particular aspect it relates to processes for the preparation of microspheres of a polymer and a drug and to products produced thereby.

Broadly, the microspheres of this invention may be described as: microcapsules of a core material, e.g., drug, and a polymer wherein the polymer coats a drug particle; or microprills which are homogeneous mixtures of a core material, e.g., drug, and a polymer. The processes of this invention are directed to the preparation of microspheres by novel phase separation techniques.

Microencapsulation by phase separation techniques is known in the prior art. For example, U.S. Pat. No. 3,242,051 describes a microencapsulation process for coating particles by phase separation in a nonaqueous medium.

Various prior art publications have reviewed microencapsulation by phase separation and these include:

"Microencapsulation" by Louis A. Luzzi in Journal of Pharmaceutical Sciences, Vol. 59, No. 10, 1367–1376 (1970); "Microencapsulation" by Wolfgang Sliwka in Angew. Chem. Internat. Edit., Vol. 14, No. 8, 539–550, (1975); "A Review of Microencapsulation" by Nawal N. Salib in Pharm. Ind., Vol. 39, No. 5, 506–512, (1977); "Microencapsulation, Processes and Applications," edited by Jan E. Vandegaer, Plenum Press, N.Y., 1974; "Microencapsulation," edited by J. R. Nixon, Marcel Dekker, Inc., 1976.

The techniques set forth in these publications have in common the fact that the core material of the desired particle size is dispersed in a continuous phase which is comprised the polymeric wall material in solution. The polymeric material is then deposited on the core material by gradual precipitation of the polymer. This is achieved either by the use of precipitants, by changes in temperature or by removal of the solvent by dilution or distillation.

One application of temperature was reported in U.S. Pat. No. 3,531,418 wherein a mixture of polymer and core material was heated to dissolve the polymer and then slowly cooled to room temperature to allow the polymer to separate and encapsulate the core material. Another example of the use of temperature was reported in U.S. Pat. No. 3,657,144 wherein a mixture of polymer and core material was heated in a volatile solvent for the polymer with an appreciably less volatile nonsolvent. Evaporation of the volatile solvent by heating caused the polymer to separate and coat the core material.

U.S. Pat. No. 3,773,919 broadly describes the microencapsulation of a drug with a biodegradable polymer (polylactide polymer) by a phase separation process (similar to that disclosed earlier in U.S. Pat. No. 3,242,051). The process consists of (1) suspending drug particles in a solvent system in which the polymer is soluble but the drug is not soluble; and (2) adding an agent incompatible with the polymer-solvent system, such as an incompatible polymer, a nonsolvent for the polymer, or a salt, or to vary the conditions such as temperature or pressure, to precipitate the polymer thus coating the drug particles.

The prior art use of temperature for preparing microcapsules by phase separation had been limited to room temperature or higher. None of the prior art cited discloses the use of low temperature phase separation process.

Prior to U.S. Pat. No. 3,773,919 it was disclosed in U.S. Pat. No. 3,336,155 that it is often impossible to obtain discrete microencapsulated particles by a phase separation process and that it was necessary to incorporate a mineral silicate (e.g., talc) during the addition of a nonsolvent to minimize the deleterious adhesion and coalescense of the encapsulated particles. However, these products would be unacceptable in many applications, for example, in pharmaceutical injectable formulations.

U.S. Pat. No. 3,887,699 discloses the preparation of homogeneous mixtures of a polymer and a drug which are formed by mixing the drug and biodegradable polymer in a suitable solvent to form a homogeneous solution. The solvent is then removed and the residue is subsequently formed into the desired shape by molding, extruding, etc.

Thus there is no satisfactory procedure reported in the prior art for obtaining discrete, spherical microspheres of polymer and a core material by phase separation which would be suitable in a broad range of applications.

SUMMARY OF THE INVENTION

Broadly, this invention provides low temperature, e.g., $-40°$ to $-100°$ C., phase separation processes for the preparation of microspheres, e.g., microcapsules and microprills. The microcapsules of this invention comprising a polymer and a core material, e.g., drug, may be prepared by dissolving the polymer in a solvent in which the drug is not soluble;

lowering the temperature of the polymer-solvent system to about $-40°$ to about $-100°$ C.;

adding the drug particles; and adding a phase separation agent, e.g., a nonsolvent with or without an incompatible polymeric phase inducing agent to the polymer-solvent-drug system to precipitate the polymer and coat the drug particles.

The microprills of this invention which comprise discrete homogeneous mixture of a polymer and a core material, e.g., drug, may be prepared by dissolving the polymer and core material in a solvent, lowering the temperature of resultant solution to about $-40°$ to $-100°$ C., and adding a polymer-drug nonsolvent with or without an incompatable phase inducing agent to the solution to precipitate discrete microprills. The term core material refers to the active agent in the microprill.

The essential feature of this invention is the use of very low temperatures, $-40°$ to $-100°$ C., with a phase separation agent, to stabilize the polymer against uncontrolled, massive agglomeration during phase separation.

As will be appreciated by those skilled in the art, in the preparation of microcapsules of this invention, it is not critical at what stage of the process that the process temperature is lowered to −40° to −100° C., but it is only critical that it be at the desired low temperature prior to phase separation.

The same criteria holds for the preparation of the microprills of this invention in that it is only critical that a temperature of −40° to −100° C. be achieved prior to phase separation.

The term nonsolvent is meant to conventionally include both nonsolvent phase separation agents and nonsolvents used as hardening agents, when used subsequent to an incompatible polymeric phase inducing agent. When used as a hardening agent, it is understood that nonsolvent addition takes place at the process temperature of −40° to −100° C.

DESCRIPTION OF THE PREFERRED EMBODIMENTS

The formation of microcapsules of this invention is based on polymer phase separation phenomena. When a phase separation agent is initially added to a polymer solution in which solid drug particles are dispersed, the polymer which separates is in a liquid phase and is deposited as a coating on the dispersed drug particles. Further addition of phase separation agent causes the coating to harden as a capsule wall completely surrounding the drug particle. By varying conditions, the coated drug particles can remain as individual capsules or agglomerate in a controlled manner to form aggregate microcapsules of larger size. Undesirable massive agglomeration occurs when adhesion and coalescence of the encapsulated particles develop precipitiously beyond control. The present low temperature process renders the microspheres sufficiently firm to avoid undesired agglomeration.

The homogeneous microprills of this invention are also formed by the phase separation phenomena. When a nonsolvent for both the polymer and the drug is added to a homogeneous solution of polymer and drug, both the polymer and the drug phase out together to form homogeneous microprills. Depending on conditions, they can remain as individual spheres or be allowed to agglomerate in a controlled manner to form larger homogeneous microprills.

Depending on the end use of the product, it may be desirable to prepare aggregate microspheres larger than the individual microspheres. For example, for controlled release of drug suitable for parenteral administration, the size of the microspheres should be large enough to provide adequate duration of release yet small enough to not restrict passage through the standard syringe needles employed. Thus, the desired size would be about 150 microns for a No. 20 gauge needle.

For other applications it may be desirable to allow controlled agglomeration to form microspheres larger or smaller than 150 microns.

The temperature range for the process of this invention is from about −40° to −100° C., preferably −40° to −75° C., more preferably −50° to −70° C.

As noted above, the prior art use of temperature for preparing microcapsules by phase separation had been limited to room temperature or higher. This invention is based on the unexpected discovery that discrete, spherical microspheres of a polymer and a core material can be obtained when the phase separation process is conducted at very low temperatures. The polymer, as it is being phased out of solution by the nonsolvent, must be sufficiently fluid to encapsulate the dispersed drug particles, or assume a spherical configuration in the case of microprills, and still be sufficiently firm to avoid massive agglomeration. This requirement is satisfied at the very low temperatures set forth above.

The upper temperature limit is dictated by the ability to avoid massive agglomeration. In general, operating at a lower temperature would provide more margin against this undesired agglomeration. The lower temperatures are limited by the freezing point of the solvent, nonsolvent or mixture of the two which are utilized.

Natural and synthetic polymers may be used in the process of this invention for the preparation of microspheres. For example, the polymers may include cellulosic polymers, polyvinyl acetate, polyvinyl alcohol, polyvinyl chloride, natural and synthetic rubbers, polyacrylates, polystyrene and the like. When the microspheres of this invention are intended for injectable pharmaceutical applications, biodegradable polymers such as polylactic acid, polyglycolic acid, polyhydroxybutyric acid and the like and copolymers thereof may be utilized.

The core material of the microsphere may be those substances whose surface is amenable to be coated with the polymer utilized. The core material of the microspheres prepared by the process of this invention may be agricultural agents such as insecticides, fungicides, herbicides, rodenticides, pesticides, fertilizers, and viruses for crop protection and the like; cosmetic agents such as deodorants, fragrances and the like; food additives such as flavors, oils, fats and the like; and pharmaceutical agents. Since many of the biologically active materials are heat-sensitive, the process of this invention provides a particular advantage in this respect.

Pharmaceutical agents, e.g., drugs, are especially preferred core materials and the invention will be further discribed using drugs as the core material. These drugs may be in free base form or in the form of their nontoxic pharmaceutically acceptable acid addition salts. Representative of such salts are the hydrochloride, sulfate, phosphate, succinate, benzoate, acetate, pamoate, fumarate, mesylate and the like. Among the pharmaceutical agents which may be utilized are the following:

Gastro-intestinal therapeutic agents

Antacids

Aluminum Hydroxide
Calcium Carbonate
Magnesium Carbonate
Sodium Carbonate

Non-Steroidal Anti-fertility agents

Parasymphathomimetic agents

Psychotherapeutic Agents

Major tranquilizers chloropromazine HCl
clozapine
mesoridazine
metiapine
reserpine
thioridazine Minor tranquilizers chlordiazepoxide
diazepam
meprobamate temazepam

Rhinological Decongestants

Sedative-hypnotics codeine
phenobarbital
sodium pentabarbital
sodium secobarbital

Steroids

Estrogens

Diethyl stilbestrol
17-β-estradiol
Estrone
Ethinyl estradiol

Progestational agents

Chlormadinone
Ethisterone
Megestrol
Melengestrol
Norethindrone
Norethynodrel

Sulfonamides

Sympathomimetic agents

Vaccines

Vitamins and nutrients essential amino acids
essential fats

Anti-malarials 4-aminoquinolines
8-aminoquinolines
pyrimethamine

Anti-migraine Agents

Mazindol
Phentermine

Anti-Parkinson

Levodopa

Antispasmodics

Atropine
Methscopolamine bromide

Antispasmodics and Anticholinergics

Bile therapy
Digestants
Enzymes

Antitussives dextromethorphan
noscapine

Bronchodilators

Cardiovascular Agents

Anti-hypertensives
Rauwolfia alkaloids
Coronary vasodilators
nitroglycerin
Organic nitrates
pentaerythritoltetranitrate

Electrolyte replacement potassium chloride

Ergot-Alkaloids

Ergotamine with and without caffeine
Hydrogenated ergot alkaloids
dihydroergocristine methanesulfate
dihydroergocornine methanesulfonate
dihydroergokroyptine methansulfate and combinations

Alkaloids

Atropine sulfate
Belladonna
Hyoscine hydrobromide

Analgetics

Narcotics codeine
dihydrocodienone
meperidine
morphine

Non-narcotics salicylates
aspirin
acetaminophen
d-propoxyphene

Antibiotics

Cephalosporins
Penicillins
ampicillin
penicillin G
Tetracyclines

Anti-cancer agents

Anti-convulsants mephenytoin
phenobarbital
trimethadione

Anti-emetics

Thiethylperazine

Antihistamines

Chlorophenazine
Dimenhydrinate
Diphenhydramine
Perphenazine
Tripelennamine

Anti-inflammatory agents hormonal
hydrocortisone
prednisolone
prednisone
non-hormonal
allopurinol
aspirin
indomethacin
Phenylbutazone The polymer-drug compositions may also include controlled release injectable, oral and topical formulations. Other pharmaceutical applications may include taste-masking of bitter drugs, separation of incompatible drugs, and the protection of drugs from moisture, light and air.

Multiple encapsulated microcapsules may be prepared by the low temperature phase separation process of this invention by utilizing a dispersion of preformed microcapsules or homogeneous microprills in a polymer solution. In certain cases it may be necessary to lower the temperature (−40° to −100° C.) of the polymer solution prior to the introduction of the preformed microspheres to avoid dissolving the preformed microspheres in the polymer solution. This concept is especially useful for reducing the initial release rate, and therefore increases the duration of release, by depositing a layer of polymer as a barrier on preformed microspheres. This technique can be extended to create multilayered microspheres.

Multiple encapsulation can also be used to produce new microcapsules formed by controlled aggregation of one or more heterogeneous, preformed microspheres with or without one or more free drugs. For example, two or more drugs can be microencapsulated separately, either because of incompatibility or lack of a common microencapsulation procedure suitable for all the component drugs. These preformed microcapsules can be combined and dispersed in a polymer solution for a subsequent microencapsulation to produce new microcapsules containing the previously encapsulated drug particles. Such compartmentalized microcapsules offer an advantage over a physical mixture in that uniformity is maintained by avoiding any uneven settling of the components upon storage.

Another application for compartmentalized microcapsules would be to segregate one or more reactants for subsequent reaction upon demand. Release for reaction can be effected by pressure rupture, passage of time, exposure to water, air, light, heat or other triggering mechanism.

For the preparation of microcapsules, the solvent selected must dissolve the polymer but not the dispersed core material, e.g., drug particles. This requirement is more easily met at low temperatures since drug solubility is usually decreased at lower temperature. For the preparation of homogenous microprills, the solvent must dissolve both polymer and drug substance at the very low temperature. For either microcapsules or microprills, the solvent should be relatively volatile, inert to both polymer and drug, have a freezing point sufficiently below the required operating temperature and also be miscible with the nonsolvent at that low temperature.

Examples of solvent for the biodegradable polylactic acid polymer and its copolymers include benzene, toluene, xylene, chloroform, methylene chloride, acetone, ethyl acetate, tetrahydrofuran, dioxane, hexafluoroisopropanol and the like.

It is not necessary to be limited to a single solvent system and there may be circumstances warranting a mixed solvent. An illustration of this would be to depress the freezing point of a preferred solvent, for example the addition of toluene (f.p. −95° C.) to chloroform (f.p. −63° C.) to enable operating below −63° C. Another situation is where the drug particles for encapsulation have some solubility in the solvent of choice for the polymer. Sufficient amount of another solvent may be added to minimize drug solubility without affecting polymer solubility. A variation of this is where there is no common solvent for both the polymer and the drug. A mixed system may act as a common solvent for the preparation of homogeneous microprills. Similar modifications will be apparent to those skilled in the art.

The choice of nonsolvent for the preparation of the microspheres of this invention is such that it must be a nonsolvent for both the polymer and the core material. This requirement is somewhat attenuated since the solubility of polymer and drug is usually decreased at lower temperature. Drug insolubility is further enhanced after it is in the polymer matrix of the microsphere. Additionally, the nonsolvent should be relatively volatile or easily removed by washing with another volatile nonsolvent, inert to both polymer and drug, have a freezing point sufficiently below the required operating temperature and also be miscible with the solvent at that low temperature.

Although both nonpolar and polar nonsolvents may be used, polar nonsolvents are preferred. Examples of nonpolar nonsolvent include the alkane hydrocarbons (e.g., hexane, heptane, cyclohexane). Examples of polar nonsolvent include water, alcohols (e.g., isopropanol, isobutyl alcohol), ethers, polyhydric alcohols (e.g., 1,2-glycols such as propylene glycol; 1,3-glycols such as trimethylene glycol; trihydric alcohols such as glycerol) and ethers and esters of the polyhydric alcohols. Polyhydric alcohols are especially preferred as the nonsolvent for producing microspheres of larger diameters which would provide longer duration of release of the core material. Other nonsolvent which may be used are the fluorocarbons (e.g., Freon-11, Freon-113 from DuPont).

The nonsolvent need not be limited to a single component system and mixed nonsolvent systems may be used. For example, to depress the freezing point of a nonsolvent to allow operating at a very low temperature. Another example is where the drug substance has some solubility in the preferred nonsolvent for the polymer. Sufficient amount of another nonsolvent may be added to minimize drug solubility, e.g., the addition of a nonpolar nonsolvent like heptane to reduce solubility of a drug in isopropanol. A co-nonsolvent may also be used to maintain miscibility between the preferred nonsolvent and the preferred solvent. Similar modifications will be apparent to those skilled in the art.

It will be understood by those skilled in the art that the polymeric phase inducing agent of this invention must be incompatible with both the coating polymer and the core material, e.g., drug and misible with both the solvent and the nonsolvent. Among the polymeric phase inducing agents which may be used are polybutadiene, polydimethylsiloxane, and the like.

EXAMPLE 1

A solution of 1.0 g. poly(D,L-lactic acid) polymer (intrinsic viscosity of 2.32 in hexafluoroisopropanol at 25° C.) in 50 ml. toluene was cooled to about −65° C. in a dry ice-isopropanol bath. Micronized Mellaril pamoate (thioridazine, Sandoz, Inc.) (0.5 g.) was dispersed in the polymer solution with stirring at 160 rpm. Isopropanol (150 ml) was added dropwise to the dispersion at the rate of one hour for the first 50 ml. and 0.5 hour for the remaining 100 ml. The dry ice bath was removed and the microcapsules were allowed to settle before decanting the supernatant. The product was washed twice with heptane, dried and weighed 1.15 (77% yield). Microscopic examination (210X) showed that the product was spherical microcapsules with diameter of about 25–50 microns.

EXAMPLE 2

This Example was conducted at room temperature, following the microencapsulation procedure described in U.S. Pat. No. 3,773,919.

Micronized Mellaril pamoate (0.5 g.) was dispersed with stirring at 170 rpm in a solution of 1.0 g. poly(D,L-lactic acid) polymer in 150 ml. of 20:130 cyclohexanetoluene. The drug particles are softened in toluene and the addition of cyclohexane in the solvent system avoided this without affecting polymer solubility.

After 14 ml. of cyclohexane (total=21% cyclohexane) was added dropwise in 10 minutes to the dispersion, small clumps began to precipitate. These formed a single, large mass when 18 ml. was added (total=23% cyclohexane). A total of 100 ml. of nonsolvent was added. The precipitated material was manually broken into pieces, washed with cyclohexane then heptane and dried. The product weighed 1.43 g. (95% yield).

The size of the small pieces was dependent on the effort expended in manually breaking up the precipitated mass. Discrete, spherical microcapsules were not obtained.

EXAMPLE 3

The procedure of Example 1 was followed except that 150 ml. of isobutyl alcohol (2-methyl-1-propanol) was used. This was followed by the addition of 50 ml. heptane in ten minutes to facilitate the capsule wall hardening process. The yield was 1.37 g. (91%) of spherical microcapsules with a diameter of 20-30 microns.

EXAMPLE 4

The procedure of Example 1 was followed except that 150 ml. of 50:50 (v/v) n-propanol/isopropanol was added at the rate of 40 minutes for the first 50 ml. and 35 minutes for the remaining 100 ml. This was followed by the addition of 50 ml. heptane. The yield was 1.42 g. (95%) of spherical microcapsules with a diameter of 20–40 microns.

EXAMPLE 5

The procedure of Example 1 was followed except that 150 ml. of heptane was used instead of isopropanol, and the dispersion was allowed to warm up to room temperature over four hours with constant stirring. The product weighed 1.22 g. (81% yield). Microcapsules of 50-200 micron size were obtained.

EXAMPLE 6

The procedure of Example 1 was followed except that 150 ml. of 15:85 (v/v) heptane/isopropanol was used instead of isopropanol. The yield was 1.1 g. (73%) of spherical microcapsules with diameter of 25-35 microns.

EXAMPLE 7

Somewhat larger microcapsules were prepared when propylene glycol/isopropanol was used as the nonsolvent. A solution of 1.0 g. poly(D,L-lactic acid) polymer (intrinsic viscosity of 2.32 in hexafluoroisopropanol at 25° C.) in 50 ml. toluene was cooled to −50° C. (slightly warmer temperature was used to avoid freezing the propylene glycol, f.p. −59°) in a dry ice-isopropanol bath. Micronized Mellaril pamoate (0.5 g.) was dispersed in the polymer solution with stirring at 160 rpm. A solution (100 ml.) of 33:67 (v/v) propylene glycol/isopropanol was added dropwise to the dispersion at the rate of one hour for the first 50 ml. and 20 minutes for the remaining 50 ml. This was followed by the addition of 50 ml. heptane in 10 minutes. The dry ice bath was removed and the microcapsules were allowed to settle before decanting the supernatant. The product was washed once with 1:1 (v/v) heptane/isopropanol, twice with isopropanol then twice with heptane. After a brief air-drying, microscopic examination showed that the product was well-formed, spherical microcapsules with diameter of 50-150 but mostly 100-125 microns. However, after drying in the vacuum oven at 50°-60° C. for four hours, the capsules decreased to about 50 to 75 microns and became crenated. The dried product weighed 1.16 g. (77% yield).

EXAMPLE 8

A homogeneous solution of 1.0 g. poly(D,L-lactic acid) polymer and 0.5 g. Mellaril pamoate in 50 ml. of 1:1 (v/v) toluene/chloroform was cooled to −65° C. with stirring at 160 rpm. The addition of toluene allowed operating at −65° without freezing the chloroform (f.p. −63° C.).

Isopropanol (150 ml.) was added dropwise at the rate of 1.5 hours for the first 100 ml. and 0.5 hour for the remaining 50 ml. The product was washed twice with heptane, dried and weighed 1.4 g. (93% yield). Microscopic examination showed that the resultant homogeneous microprills were 20-50 microns in diameter.

EXAMPLE 9

Larger microprills were prepared when propylene glycol/isopropanol was used as the nonsolvent. A homogeneous solution of 1.0 g. poly(D,L-lactic acid) polymer and 0.5 g. Mellaril pamoate in 50 ml. chloroform was cooled to −50° C. with stirring at 160 rpm. A solution (100 ml.) of 35:65 (v/v) propylene glycol/isopropanol was added dropwise to above solution at the rate of 70 minutes for the first 50 ml. and 20 minutes for the remaining 50 ml. This was followed by the addition of 50 ml. heptane in 15 minutes.

After decanting the supernatant, the product was washed once with 1:1 (v/v) heptane/isopropanol, twice with isopropanol then twice with heptane. Upon drying, it weighed 1.44 g. (96% yield). Microscopic examination showed that the resultant homogeneous microprills were 100-125 microns in diameter.

EXAMPLE 10

A solution of 0.22 g. poly(D,L-lactic acid) polymer in 50 ml. toluene was cooled to about −65° C. in a dry ice-isopropanol bath. Microcapsules (0.75 g., about 35 microns, previously prepared as in Example 1 to contain 33% Mellaril pamoate) were dispersed in the polymer solution with stirring at 160 rpm. Isopropanol (150 ml.) was added dropwise to the dispersion and the rest of the procedure of Example 1 was followed. The yield was 0.73 g. (75%). Careful microscopic examination (210X) showed a thin, transparent wall of poly(D,L-lactic acid) polymer surrounding each microcapsule.

EXAMPLE 11

The data in this example showed that the microencapsulated drug Mellaril pamoate has slower release rate than the non-encapsulated Mellaril pamoate. Furthermore, the double-encapsulated Mellaril pamoate microcapsules (25-40 microns) showed significantly reduced initial release rate compared to the single-encapsulated microcapsules (50–200 microns). The reason for the shorter release duration of the double-encapsulated material is due to its smaller size.

| | % Release | | |
|---|---|---|---|
| Hour | Non-Encapsulated Drug | Single Encapsulated Drug Example 5. | Double Encapsulated Drug Example 10. |
| 1 | 48 | 42 | 23 |
| 4 | — | 42 | 37 |
| 6 | — | 44 | 46 |
| 24 | 100 | 65 | 78 |
| 30 | — | 75 | 100 |
| 48 | — | 77 | — |
| 72 | — | 100 | — |

Procedure

A sample containing the equivalent of 4.0 mg. Mellaril pamoate was placed in a dissolution flask containing 1000 ml. of pH 7.4, 0.2 M phosphate buffer. The mixture was maintained at 37° C. with stirring at 500+ rpm. Aliquots were withdrawn at various time points and the absorbance was measured at 224 nm. with an ultraviolet spectrophotometer. The percent drug released was based on the maximum absorbance measured for each sample.

EXAMPLE 12

A solution of 0.25 g. poly(D,L-lactic acid) polymer in 50 ml. toluene was cooled to about −65° C. in a dry iceisopropanol bath. Microprills (0.75 g., 100–150 microns, previously prepared as in Example 9) were dispersed in the polymer solution with stirring at 160 rpm. The procedure of Example 1 was followed except that 100 ml. of 20:80 (v/v) heptane/isopropanol followed by 50 ml. of heptane was used. The yield was 0.89 g. (89%) of double-encapsulated microprills of 100–150 microns diameter.

EXAMPLE 13

A dispersion of 0.6 g. bromocriptine mesylate (Sandoz, Inc.) in a solution of 1.4 g. poly(D,L-lactic acid) polymer in 55 ml. of toluene was stirred at 140 rpm with cooling to −70° C. in a dry ice-isopropanol bath. The procedure of Example 1 was followed except that 100 ml. of 25:75 (v/v) heptane/isopropanol followed by 50 ml. of heptane was used. The yield was 1.71 g. (86%) of spherical microcapsules of 15–40 microns diameter. Microscopic examination under polarized light of the microcapsules immersed in oil showed that the microcapsules contained drug particles whose iridescence was visible through the capsule wall.

EXAMPLE 14

A dispersion of 1.0 g. pindolol (Sandoz, Inc.) (well-pulverized with mortar and pestle) in a solution of 1.0 g. poly(D,L-lactic acid) polymer in 100 ml. of toluene was stirred at 150 rpm with cooling to −70° C. in a dry ice-isopropanol bath. The procedure of Example 1 was followed except that 50 ml. of 5:95 (v/v) heptane/isopropanol followed by 50 ml. of heptane was used. The yield was 1.82 g. (91%) of spherical microcapsules of 50–75 microns diameter. Microscopic examination under polarized light of the microcapsules immersed in oil showed that the microcapsules contained drug particles whose iridescence was visible through the capsule wall.

EXAMPLE 15

A dispersion of 1.0 g. dihydroergotamine mesylate (Sandoz, Inc.) (well-pulverized with mortar and pestle) in a solution of 1.0 g. poly(D,L-lactic acid) polymer in 100 ml. of toluene was stirred at 140 rpm with cooling to −70° C. in a dry ice-isopropanol bath. The procedure of Example 1 was followed except that 100 ml. of isopropanol followed by 100 ml. of toluene was used. The yield was 1.98 g. (99%) of spherical microcapsules of 75–150 microns diameter. Microscopic examination under polarized light of the microcapsules immersed in oil showed that the microcapsules contained drug particles whose iridescence was visible through the capsule wall.

What is claimed is:

1. In a process for the preparation of microspheres having a particulate core material encapsulated by a polymeric coating wherein the polymer is dissolved in a solvent in which the core material is not soluble and the polymer is precipitated by phase separation to encapsulate the core material by the addition of phase separation agent to the polymer-core material-solvent system; the improvement which comprises lowering the temperature of said system from about −40° to −100° C. and then adding the phase separation agent to the polymer-core material-solvent system to cause phase separation of the polymer.

2. The process according to claim 1 wherein the temperature is from about −40° to −75° C.

3. The process according to claim 2 wherein the temperature is from about −50° to −70° C.

4. The process according to claim 1 wherein the core material is a drug.

5. The process according to claim 4 wherein the polymer is selected from the group consisting of cellulosic polymers, polyvinyl acetate, polyvinyl alcohol, polyvinyl chloride, polyacrylates, polystyrene, polylactic acid, polyglycolic acid, polyhydroxybutyric acid and copolymers thereof.

6. The process according to claim 5 wherein the polymer is polylactic acid.

7. The process according to claim 6 wherein the core material is selected from the group consisting of thioridazine, bromocriptine, pindolol or dihydroergotamine, or acid addition salts thereof.

8. The process according to claim 6 wherein the solvent is selected from the group consisting of benzene, toluene, xylene, chloroform, methylene chloride, acetone, ethyl acetate, tetrahydrofuran, dioxane, hexafluoroisopropanol and mixtures thereof.

9. The process according to claim 8 wherein the phase separation agent is a nonsolvent selected from the group consisting of water, monohydric alcohols, dihydric alcohols, trihydric alcohols, ethers, polyhydric alcohol ethers, polyhydric alcohol esters, alkane hydrocarbons, fluorocarbons and mixtures thereof.

10. The process according to claim 9 wherein the nonsolvent is selected from the group consisting of isopropyl alcohol, isobutyl alcohol, propylene glycol, heptane, cyclohexane and mixtures thereof.

11. A process for the preparation of microspheres having a homogeneous mixture of a polymer and core material which comprises,
   dissolving the polymer and core material in a solvent,
      lowering the temperature of the resultant solution to about −40° to −100° C., and adding a polymer-core material phase separation agent to the solution to precipate microspheres of a homogeneous mixture of the polymer and core material.

12. The process according to claim 11 wherein the temperature is from about −40° to −75° C.

13. The process according to claim 12 wherein the temperature is from about −50° to −70° C.

14. The process according to claim 11 wherein the core material is a drug.

15. The process according to claim 14 wherein the polymer is selected from the group consisting of cellulosic polymers, polyvinyl acetate, polyvinyl alcohol, polyvinyl chloride, polyacrylates, polystyrene, polylactic acid, polyglycolic acid, polyhydroxybutyric acid and copolymers thereof.

16. The process according to claim 15 wherein the polymer is polyacetic acid.

17. The process according to claim 16 wherein the core material is selected from the group consisting of thioridazine, bromocriptine, pindolol or dihydroergotamine, or an acid addition salt thereof.

18. The process according to claim 16 wherein the solvent is selected from the group consisting of benzene, toluene, xylene, chloroform, methylene chloride, acetone, ethyl acetate, tetrahydrofuran, dioxane, hexafluoroisopropanol and mixtures thereof.

19. The process according to claim 18 wherein the phase separation agent is a nonsolvent selected from the group consisting of water, monohydric alcohols, dihydric alcohols, trihydric alcohols, ethers, polyhydric alcohol ethers, polyhydric alcohol esters, alkane hydrocarbons, fluorocarbons and mixtures thereof.

20. The process according to claim 19 wherein the nonsolvent is selected from the group consisting of isopropyl alcohol, isobutyl alcohol, propylene glycol, heptane, cyclohexane and mixtures thereof.

21. In a process for the encapsulation of preformed microspheres having a particulate core material encapsulated by a polymeric coating wherein the polymer is dissolved in a solvent in which the microsphere is not soluble and the polymer is precipated by phase separation to encapsulate the microsphere by the addition of phase separation agent to the polymer-microsphere-solvent system; the improvement which comprises lowering the temperature of said system from about −40° to −100° C. and then adding the phase separation agent to the polymer-microsphere-solvent system to cause phase separation of the polymer.

22. The process according to claim 21 wherein the temperature is from about −40° to −75° C.

23. The process according to claim 22 wherein the temperature is from about −50° to −70° C.

24. The process according to claim 21 wherein the microsphere is a preformed microcapsule wherein a drug is encapsulated by a polymeric coating.

25. The process according to claim 24 wherein the preformed microsphere polymer is polylactic acid and the microencapsulated drug is selected from the group consisting of thioridazine, bromocriptine, pindolol or dihydroergotamine, or an acid addition salt thereof.

26. The process according to claim 25 wherein the coating polymer is selected from the group consisting of cellulosic polymers, polyvinyl acetate, polyvinyl alcohol, polyvinyl chloride, polyacrylates, polystyrene, polylactic acid, polyglycolic acid, polyhydroxybutyric acid and copolymers thereof.

27. The process according to claim 26 wherein the coating polymer is polylactic acid.

28. The process according to claim 27 wherein the solvent is selected from the group consisting of benzene, toluene, xylene, chloroform, methylene chloride, acetone, ethyl acetate, tetrahydrofuran, dioxane, hexafluoroisopropanol and mixtures thereof.

29. The process according to claim 28 wherein the phase separation agent is a nonsolvent selected from the group consisting of water, monohydric alcohols, dihydric alcohols, trihydric alcohols, ethers, polyhydric alcohol ethers, polyhydric alcohol esters, alkane hydrocarbons, fluorocarbons and mixture thereof.

30. The process according to claim 29 wherein the nonsolvent is selected from the group consisting of isopropyl alcohol, isobutyl alcohol, propylene glycol, heptane, cyclohexane and mixtures thereof.

31. The process according to claim 21 wherein the microsphere is a preformed microprill wherein a core material is in homogeneous mixture with a polymer.

32. The process according to claim 31 wherein the temperature is from about −40° to −75° C.

33. The process according to claim 32 wherein the temperature is from about −50° to −70° C.

34. The process according to claim 31 wherein the microsphere is a preformed microprill wherein a drug is in homogeneous mixture with a polymer.

35. The process according to claim 34 wherein the preformed microprill polymer is polylactic acid and the drug is selected from the group consisting of thioridazine, bromocriptine, pindolol or dihydroergotamine, or an acid addition salt thereof.

36. The process according to claim 35 wherein the coating polymer is selected from the group consisting of cellulosic polymers, polyvinyl acetate, polyvinyl alcohol, polyvinyl chloride, polyacrylates, polystyrene, polylactic acid, polyglycolic acid, polyhydroxybutyric acid and copolymers thereof.

37. The process according to claim 36 wherein the coating polymer is polylactic acid.

38. The process according to claim 37 wherein the solvent is selected from the group consisting of benzene, toluene, xylene, chloroform, methylene chloride, acetone, ethyl acetate, tetrahydrofuran, dioxane, hexafluoroisopropanol and mixtures thereof.

39. The process according to claim 38 wherein the phase separation agent is a nonsolvent selected from the group consisting of water, monohydric alcohols, dihydric alcohols, trihydric alcohols, ethers, polyhydric alcohol ethers, polyhydric alcohol esters, alkane hydrocarbons, fluorocarbons and mixtures thereof.

40. The process according to claim 39 wherein the nonsolvent is selected from the group consisting of isopropyl alcohol, isobutyl alcohol, propylene glycol, heptane, cyclohexane and mixtures thereof.

41. A process for encapsulating a plurality of heterogeneous preformed microspheres consisting essentially of, dissolving a polymer in a solvent in which the preformed microspheres are not soluble, lowering the temperature to about −40° to −100° C., adding the preformed microspheres to the polymer-solvent solution; adding a phase separation agent to the polymer-microsphere-solvent system to cause phase separation of the polymer, coating the microspheres.

42. A process for encapsulating a plurality of heterogeneous preformed microspheres consisting essentially of, dissolving a polymer and core material in a solvent in which the preformed microspheres are not soluble, lowering the temperature to about −40° to −100° C., adding the preformed microspheres to the polymer-core material-solvent solution; adding a phase separation agent to the polymer-core material-microsphere-solvent system to cause phase separation of the polymer, coating the microspheres.

43. A process for encapsulating a plurality of heterogeneous preformed microspheres with a polymer coating having core material dispersed therein consisting essentially of, dissolving a polymer in a solvent in which the core material and the preformed microspheres are not soluble, lowering the temperature to about $-40°$ to $-100°$ C., adding the core material and the preformed microspheres to the polymer-solvent solution; adding a phase separation agent to the polymer-core material-microsphere-solvent system to cause phase separation of the polymer, coating the microspheres.

44. A process for encapsulating preformed microspheres consisting essentially of, dissolving a polymer and core material in a solvent in which the preformed microspheres are not soluble, lowering the temperature to about $-40°$ to $-100°$ C., adding the preformed microspheres to the polymer-core material-solvent solution; adding a phase separation agent to the polymer-core material-microsphere-solvent system to cause phase separation of the polymer, coating the microspheres.

45. A process for encapsulating preformed microspheres with a polymer coating having core material dispersed therein consisting essentially of, dissolving a polymer in a solvent in which the core material and the preformed microspheres are not soluble, lowering the temperature to about $-40°$ to $-100°$ C., adding the core material and the preformed microspheres to the polymer-solvent solution; adding a phase separation agent to the polymer-core material-microsphere-solvent system to cause phase separation of the polymer, coating the microspheres.

* * * * *

UNITED STATES PATENT AND TRADEMARK OFFICE
CERTIFICATE OF CORRECTION

PATENT NO. : 4,166,800
DATED : Sep. 4, 1979
INVENTOR(S) : Jones W. Fong

It is certified that error appears in the above-identified patent and that said Letters Patent are hereby corrected as shown below:

Col. 12, line 9, please delete the incorrect word "toluene" and insert in its place the correct word -- heptane --.

Col. 14, line 11, please delete the word "mixture" and insert in its place the word -- mixtures --.

Signed and Sealed this

Twenty-fifth Day of December 1979

[SEAL]

Attest:

SIDNEY A. DIAMOND

Attesting Officer

Commissioner of Patents and Trademarks